United States Patent [19]

Wasnich

[11] 4,094,317
[45] June 13, 1978

[54] NEBULIZATION SYSTEM

[76] Inventor: Richard D. Wasnich, 2408 Halekoa Dr., Honolulu, Hi. 96821

[21] Appl. No.: 694,957

[22] Filed: Jun. 11, 1976

[51] Int. Cl.$^2$ .............................................. A61M 11/00
[52] U.S. Cl. ............................. 128/194; 128/DIG. 2
[58] Field of Search ............... 128/188, 194, 193, 201, 128/197, 209, 210, DIG. 2, 368; 261/DIG. 48, DIG. 65; 239/102; 259/DIG. 44

[56] References Cited

U.S. PATENT DOCUMENTS

| 2,738,172 | 3/1956 | Spiess, Jr. et al. | 259/DIG. 44 |
| 3,387,607 | 6/1968 | Gauthier et al. | 128/DIG. 2 |
| 3,404,843 | 10/1968 | Szekely | 128/194 |
| 3,490,697 | 1/1970 | Best, Jr. | 239/102 |
| 3,556,097 | 1/1971 | Wallace | 128/188 |
| 3,561,444 | 2/1971 | Boucher | 128/194 |
| 3,842,833 | 10/1974 | Ogle | 128/194 |
| 3,861,386 | 1/1975 | Harris et al. | 128/194 |
| 3,949,743 | 4/1976 | Shanbrom | 128/368 |

Primary Examiner—Robert W. Michell
Assistant Examiner—Henry J. Recla
Attorney, Agent, or Firm—Berman, Aisenberg & Platt

[57] ABSTRACT

A nebulization chamber, designed specifically for radioaerosols, for reducing mean particle size, increasing aerosol concentration, and minimizing dead space. Centrally and vertically disposed is a substantially cylindrical interaction chamber at the lower most portion of which is positioned a membrane-covered opening that serves as the liquid interface to a conventional ultrasonic nebulizer located thereunder. Positioned concentrically within the interaction chamber is an impaction sphere which acts to trap the nebulized aerosol bolus in a small, compact volume for efficient delivery to the patient. Larger aerosol particles are also impacted on the sphere to permit recovery thereof for re-nebulization. The upper end of the interaction chamber communicates with the patient's mouthpiece via a one-way valve. Positioned laterally and downstream of the interaction chamber is a valved air inlet which acts to assist movement of the aerosol bolus during initial inspiration by the patient, thereby improving delivery efficiency and minimizing dead space. An injection inlet conduit may also be provided laterally of the interaction chamber to permit measured quantities of the desired fluid to be administered.

16 Claims, 6 Drawing Figures

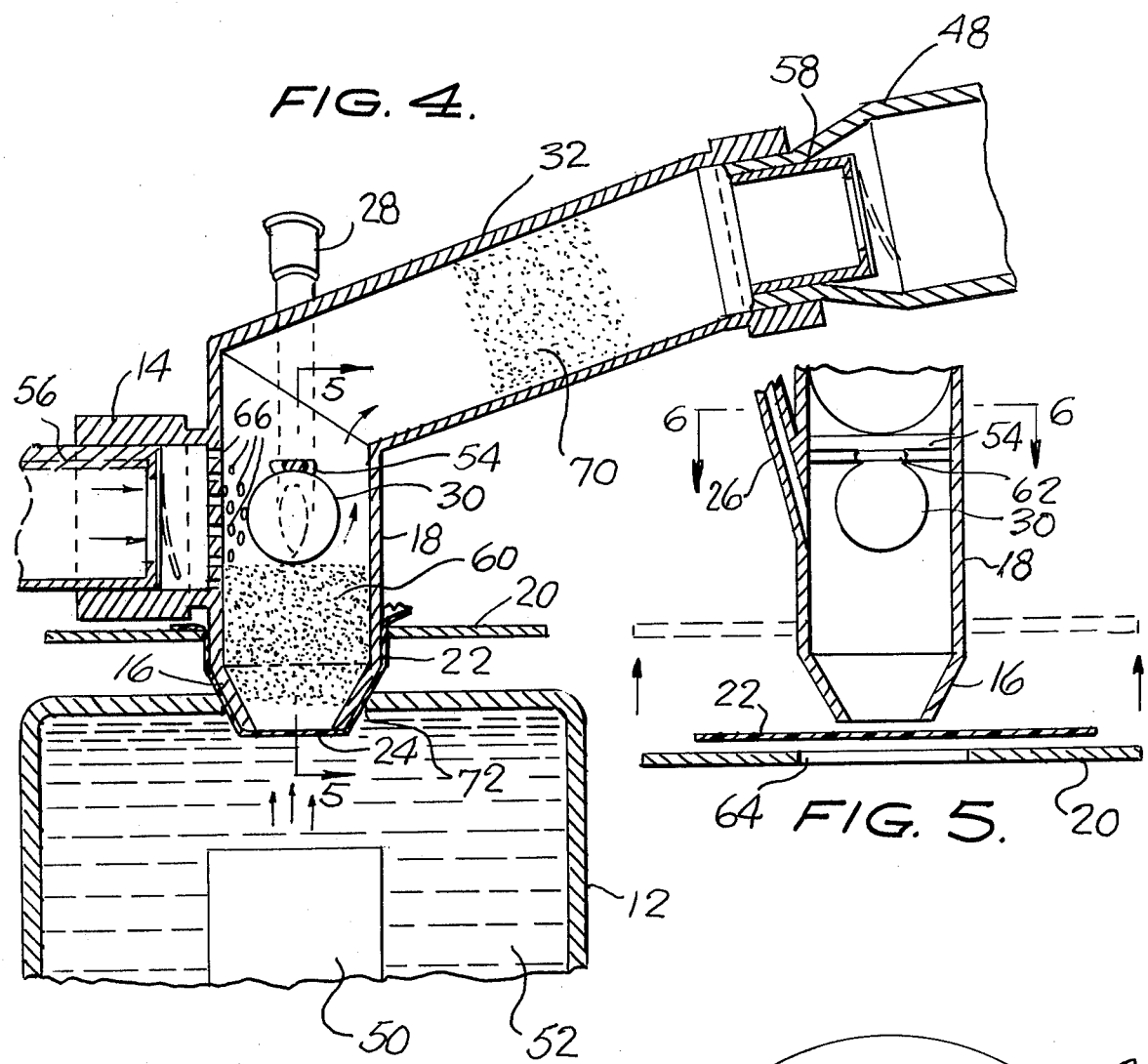
FIG. 4.
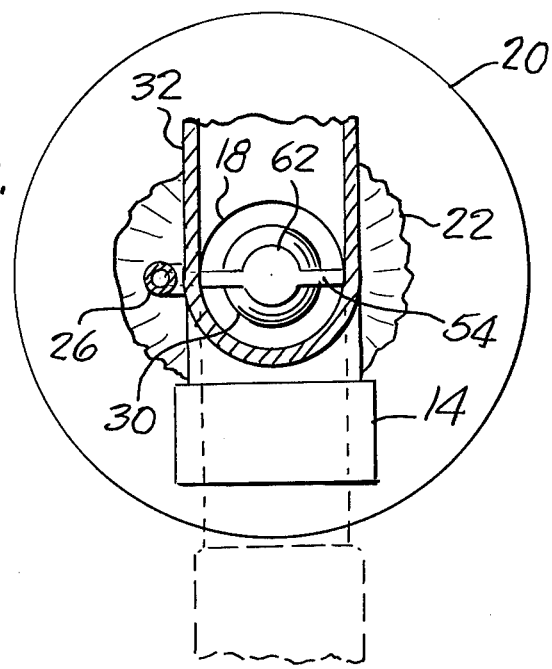
FIG. 5.
FIG. 6.

NEBULIZATION SYSTEM

BACKGROUND OF THE INVENTION

1. Field of the Invention

The present invention is related to nebulization systems utilized in medical inhalation therapy and, more particularly, is concerned with the provision of a radioaerosol nebulization chamber utilized in conjunction with an ultrasonic nebulizer for improving the efficiency of delivery of the nebulizer aerosol to the patient.

2. Description of the Prior Art

Scintigraphy is a diagnostic technique in which a two-dimensional picture of a bodily radiation source is obtained by the use of radioisotopes. Radioaerosol lung scintigraphy is one technique available for measuring the distribution of ventilation in patients having respiratory diseases, and has certain advantages over other measurement techniques. For example, radioaerosols are relatively inexpensive to produce, may be delivered at tidal volume respiration, result in high information-density aerosol inhalation images which may be obtained in multiple projections to allow precise correlation with the distribution of perfusion.

Despite such advantages, radioaerosol lung scintigraphy has not been widely adopted. A major objection to the technique is the heretofore inefficient and unpredictable nature of aerosol delivery. Larger aerosol particles tend to deposit in the trachea and major bronchi, and tend to reduce the likelihood of obtaining ventilatory distribution obtainable by other techniques.

Previous studies have indicated that the major factors effecting pulmonary distribution of aerosols are the particle size, the aerosol concentration, the air flow rate, and the airway turbulence. Such studies include, for example, an article by Taplin et al which appeared in the Journal of Nuclear Medicine, Vol. 7, pgs. 77–87, entitled "Lung Scanning Following Radioaerosol Inhalation" (1966); and an article by Mitchell in Vol. 82 of American Review of Respiratory Disease, pgs. 627–629: "Retention of Aerosol Particles in the Respiratory Tract" (1960).

Prior art patents uncovered during the course of a preliminary examination search of which I am aware include the following: U.S. Pat. Nos. 3,172,406; 3,301,255; 3,630,196; 3,744,722; 3,771,721; 3,836,079; 3,842,833; and 3,892,235. However, none of the foregoing teach devices which are specifically addressed towards the problems above-enumerated, which are peculiar to radioaerosol pulmonary ventilation distribution techniques, and which also apply to distributive techniques for non-radioactive aerosols which are also used therapeutically in various lung diseases. That is to say, common deficiencies noted with respect to the prior art devices has been their failure to provide efficient and predictable aerosol delivery to the lungs, while preventing deposition of larger aerosol particles in the trachea and major bronchi to thereby improve the overall delivery efficiency.

OBJECTS AND SUMMARY OF THE INVENTION

It is therefore a primary object of the present invention to provide a nebulization system which is adapted to provide a nebulized aerosol for inhalation therapy for a patient to be treated, and which overcomes the problems associated with prior art techniques and devices above-discussed.

Another object of the present invention is to provide a nebulization system which utilizes a standard ultrasonic transducer in combination with a nebulization delivery device which greatly improves the efficiency and predictability of aerosol delivery to the lungs.

A further object of the present invention is to provide a high-frequency ultrasonic nebulizer coupled with a nebulization chamber specifically designed for radioaerosols which permits gradual addition of a radiopharmaceutical during the delivery procedure, presents larger aerosol particles from depositing in the oropharynx and trachea, creates a higher proportion of particles in the 0.5 to 3.5 micron size range, permits recovery of larger aerosol particles for re-nebulization, and reduces dead space by trapping the generated aerosol in a small volume to result in a compact aerosol bolus which is released in the early portion of the tidal volume period.

A still further object of the present invention is to provide a nebulization delivery device which improves the efficiency and predictability of aerosol delivery for both radioactive and non-radioactive aerosols utilized in medical inhalation therapy.

An additional object of the present invention is to provide the combination of a high-frequency ultrasonic nebulizer and a delivery device which reduces overall particle size, increases aerosol concentration, and minimizes dead space, thereby providing an efficient and predictable nebulization delivery system.

The foregoing and other objects are attained in accordance with one aspect of the present invention through the provision of a nebulization system adapted to provide a nebulized aerosol for inhalation therapy of a patient to be treated. The system generally comprises an interaction chamber which, in a preferred embodiment, comprises a substantially cylindrical vertically oriented tubular member. At the bottom of the interaction chamber is positioned a reservoir means for containing a small amount of the liquid to be nebulized. The liquid may be injected into the reservoir by means of an injection inlet positioned adjacent and in communication with the interaction chamber. An ultrasonic nebulizer is disposed below the reservoir and provides an ultrasonic sound beam for nebulizing the small amount of liquid contained in the reservoir into an aerosol. Means are provided within the interaction chamber for initially maintaining the position of the aerosol therebelow for increasing the concentration thereof. Finally, an outlet conduit is positioned in communication with the interaction chamber for receiving the generated aerosol and delivering same to the mouthpiece of the patient for inhalation.

In accordance with other aspects of the present invention, the outlet conduit includes means for permitting the aerosol to be drawn therethrough only upon inhalation by the patient, which means may comprise a one-way valve. The aerosol position maintaining and concentration increasing means preferably comprises an impaction sphere positioned in the central portion of the interaction chamber above the reservoir. The sphere also serves to cause the larger particles of the aerosol to be impacted thereon and thereby be recovered for re-nebulization. An inlet conduit is disposed transversely to the interaction chamber at a position approximately adjacent the impaction sphere so as to provide a downstream impetus for movement of the aerosol subsequent to patient inhalation. The inlet conduit may also be provided with a one-way valve to control air flow from a blower preferably connected at the distal end thereof.

In accordance with still further aspects of the present invention, the reservoir comprises an interface nozzle which is connected to and extends downwardly from the lower opening of the interaction chamber. A thin membrane covers the lower opening of the nozzle for retaining the fluid to be nebulized in an adjacent relationship to the ultrasonic beam. A ring member having an aperture formed centrally therein serves as a means for retaining the thin membrane over the nozzle opening.

In accordance with yet other aspects, the present invention comprises the combination of an ultrasonic nebulizer for generating an aerosol bolus, a nebulizatin chamber which receives the aerosol bolus and transmits same to a patient to be treated, and an impaction sphere located within the nebulization chamber in the path of the aerosol bolus for increasing the concentration of the aerosol. An air inlet means is strategically connected to the nebulization chamber so as to be located downstream of the formed aerosol bolus to assist in the movement thereof to the patient after inspiration.

BRIEF DESCRIPTION OF THE DRAWINGS

Various objects, features and attendant advantages of the present invention will be more fully apreciated as the same becomes better understood from the following detailed description of the present invention when considered in connection with the accompanying drawings, in which:

FIG. 4 is a sectional view of the preferred embodiment illustrated in FIG. 3 and taken along line 4—4 thereof;

FIG. 5 is a sectional view of the embodiment illustrated in FIG. 4 taken along line 5—5 thereof and illustrating the mode of attachment of a membrane; and FIG. 6 is a sectional view of the embodiment depected in FIG. 5 and taken along line 6—6 thereof.

DETAILED DESCRIPTION OF THE PREFERRED EMBODIMENT

Figure 1:
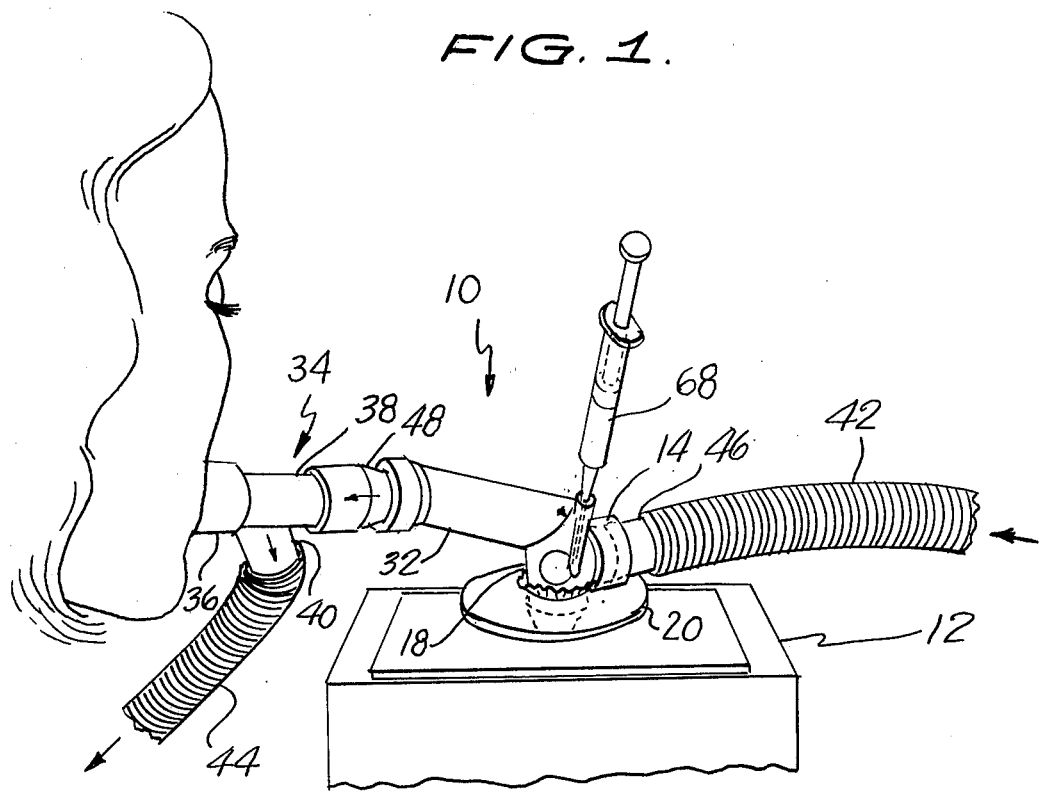
FIG. 1 is a perspective diagrammatic view which illustrates a preferred embodiment of the ultrasonic nebulization system of the present invention while in use.

Referring now to the drawings, wherein like reference numerals represent identical or corresponding parts throughout the several views, and more particularly to FIG. 1, the nebulization delivery system of the present invention comprises a nebulization chamber indicated generally by the reference numeral 10, a conventional ultrasonic nebulizer 12, and a Y-tube connector 34.

Figure 2:
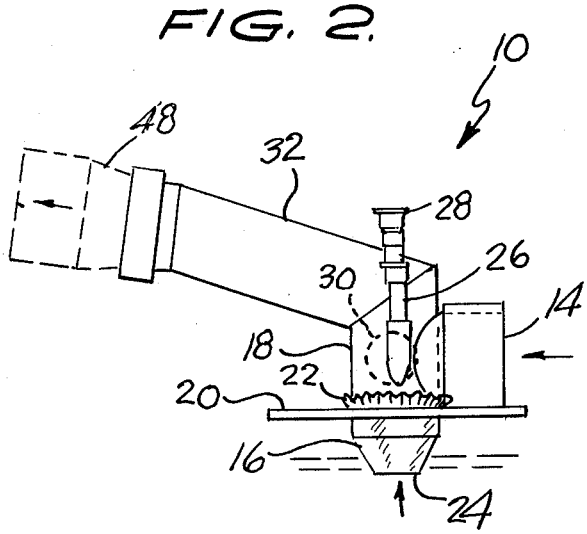
FIG. 2 is a plan view which illustrates a preferred embodiment of the nebulization chamber in accordance with the present invention.
Figure 3:
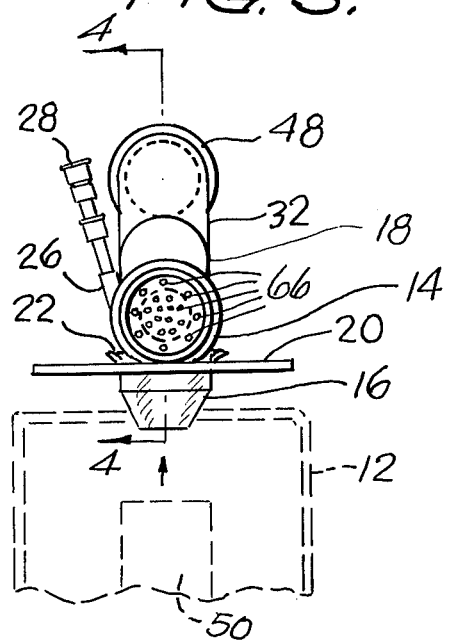
FIG. 3 is an end view of the apparatus illustrated in FIG. 2.

The nebulization chamber 10, whose construction is illustrated in more detail in FIGS. 2-6, includes an interaction chamber 18 which comprises a generally cylindrical tubular member which is vertically oriented, as illustrated in FIGS. 1 and 2, when in use. The interaction chamber 18 includes upper and lower openings, to the latter of which is connected a downwardly depending ultrasonic interface nozzle 16 which tapers inwardly to form an ultrasonic beam interface 24.

Covering the ultrasonic interface nozzle 16 is a thin membrane 22, such as cellophane or Cryovac, which is stretched taut over interface 24 by means of a ringed base 20.

Extending laterally and in communication with interaction chamber 18 is a substantially cylindrical air inlet port 14. A plurality of openings or apertures 66 are formed in the cylindrical sidewall of interaction chamber 18 adjacent port 14 in order to render same in communication with one another (see FIG. 3).

Positioned somewhat adjacent but laterally displaced from air inlet port 14 about interaction chamber 18 is an inclined tubular injection inlet conduit 26 (FIG. 5). Attached to and covering the upper end of injection inlet 26 is a flexible cap, which may be formed of rubber or the like, for sealingly receiving the needle of a syringe 68 therein (FIG. 1) The injection inlet 26 permits gradual addition of a radiopharmaceutical during the delivery procedure. This prevents the situation wherein too large a volume is provided on the interface portion 24, which impairs nebulization.

Extending angularly from the upper open end of interaction chamber 18 is an outlet conduit 32 which is connected via a connector 48 to Y-tube connector 34 which, as seen in FIG. 1, includes a patient mouthpiece 36 on one arm, an inhalation conduit 38 on another arm, and an exhalation conduit 40 on the third arm thereof.

As also viewed in FIG. 1, the exhalation conduit 40 is connected to an outlet conduit 44, which may conveniently be comprised of a flexible hose, to an exhaust hood or vent. In a like manner, the air inlet port 14 is connected via a connector 46 to an inlet conduit 42, which may also be comprised of a flexible hose, and may further be connected to an air blower to assist in the movement of the aerosol bolus formed in chamber 10.

Positioned within inlet port 14 and outlet connector 48 are a pair of one-way valves 56 and 58, respectively, which are schematically illustrated in FIG. 4. Valves 56 and 58 assist in controlling the inspiration of air to assure efficient and safe delivery of the aerosol.

From FIG. 5 the mode of attachment of the membrane 22 about the ultrasonic interface nozzle 16 may be ascertained. The ring base 20 includes a centrally formed opening 64 which is sized so as to fit in substantial close adherence to the outer circumference of interaction chamber 18. The membrane 22 is first placed adjacent the nozzle 16 and ring base 20 is thereafter drawn over the membrane and nozzle to the dotted position illustrated in FIG. 5, the resultant configuration being more clearlyillustrated in FIG. 4. The taut membrane 22 over the interface portion 24 of the nozzle 16 serves both as an excellent reservoir for the liquid medication introduced through the injection inlet 26 as well as a transmissive medium for the untrasonic sound wave generated by the ultrasonic crystal 50 of the ultrasonic nebulizer 12.

It may be seen in FIG. 4 that the lower nozzle 16 of the nebulization chamber 10 is inserted, in use, in an opening 72 formed on the top of the ultrasonic nebulizer 12. Water 52 within nebulizer 12 serves as a sound transmission medium between the membrane 22 positioned over interface 24 and the ultrasonic wavegenerating crystal 50.

Referring now more particularly to FIGS. 4-6, positioned concentrically within the cylindrical interaction chamber 18 is an impaction sphere 30. Impaction sphere 30 is mounted to a transverse support member 54 which extends between the opposing side walls of interaction chamber 18. Sphere 30 may be mounted to support member 54 by any convenient means, such as by an adhesive or glue 62. Impaction sphere 30 is preferably located near the upper opening of interaction chamber 18 and somewhat adjacent the apertures 66 which communicate the air from inlet port 14.

The impaction sphere 30 serves two primary functions. Firstly, it intersects larger aerosol particles to prevent same from being deposited in the oropharynx and the trachea. The presence of the sphere 30 in the mainstream of the aerosol creates a higher proportion of particles in the 0.5 to 3.0 micron size range, which is the size of particles that are primarily deposited in the peripheral bronchioles and alveoli. The sphere 30 thus permits recovery of the larger aerosol particles for renebulization. As a result, less of the radiopharmaceutical remains on the walls of the chamber 18 and remaining conduits, thereby improving the efficiency of the delivery process.

Secondly, the impaction sphere 30 initially traps the generated aerosol in a small volume, just below the sphere 30, as indicated generally by the reference numeral 60 in FIG. 4. The highly concentrated aerosol bolus 60 is formed while the patient (FIG. 1) is exhaling via the one-way exhaust tube 40. When inspiration commences, the bolus 60 moves through chamber 10 and into the lungs in an early phase of inspiration, resulting in highly desirable alveolar deposition, rather than undesirable mouth and orthophonics deposition. This effect is assisted by the positioning of the air inlet port 14 adjacent and downstream of the interaction chamber 18 and sphere 30 such that, when the patient first inhales, the aerosol bolus 60 is inspirated first through conduit 32, as indicated generally by reference numeral 70 of FIG. 4, and the following air received from port 14 assists in maintaining the aerosol bolus 70 intact to deliver same to the lungs in the initial inspiration stage.

According to the present invention, therefore, relatively little aerosol will be distributed in the later portion of the tidal volume. Since the later portion fills dead space only, any aerosol in such a volume will not be available for the desirable alveolar deposition, and thus will be wasted. Accordingly, the present invention, in ensuring the formation and presence of a highly concentrated bolus during initial inspiration, serves to greatly improve the overall delivery efficiency.

Outlet conduit 32 is preferably constructed as short as possible, such that the patient mouthpiece 36 may be placed, for example, within 9 cm. of the aerosol reservoir within interaction chamber 18 in order to assist in the reduction of respiratory dead space. When the present invention is utilized with radioactive aerosols, its feature of being a completely closed system becomes significant. The device 10 is preferably constructed of clear plastic, such that aerosol production and delivery may be visually monitored. Further, due to the simplified construction of the preferred embodiment, the chamber 10 may be totally immersed in strong antiseptic solutions for easy cleaning between uses.

It is seen that I have provided a nebulization chamber, designed specifically for radioaerosols, but useable with quantitative delivery of non-radioactive aerosols, which reduces mean particle size, increases aerosol concentration, and minimizes dead space. The nozzle impaction sphere, utilized in conjunction with an ultrasonic nebulizer, assists not only in recovering larger particles for renebulization, but traps the aerosol in a small, highly compact volume to increase its concentration, until the patient inhales, at which time it is drawn into the patient's mouthpiece assisted by downstream inspiration of air from a blower assembly.

In order to indicate the best mode presently contemplated for carrying out my invention, the following equipment information is provided, with the understanding that many equivalent equipment models would also be suitable. Ultrasonic nebulizer 12 may comprise of a DeVilbiss Model 900, which has a nominal frequency of approximately 4 megahertz. The one-way valves 56 and 58 may be comprised of DeVilbiss Input Check Valves No. 2-1019. Attached to input tubing 42 may be a DeVilbiss Air Supply Module No. 3100, which assists in the movement of the aerosol bolus without appreciably increasing the air flow rate (stronger blowers or positive pressure devices should preferably be avoided, since at higher flow rates more particles will be undesirably impacted in the pharynx and trachea). Typical of a radiopharmaceutical which may be utilized in syringe 68 in a technique for determining the distribution of pulmonary ventilation is 20–30 mCi. of $^{99m}$Tc-Phytate, injected in approximately 0.5 cc doses.

Obviously, numerous modifications and variations of the present invention are possible in light of the above teachings. It is therefore to be understood that within the scope of the appended claims, the invention may be practiced otherwise than as specifically described herein.

I claim as my invention:

1. A nebulization system adapted to provide a nebulized aerosol for inhalation therapy of a patient to be treated, which comprises:
    an interaction chamber having a reservoir means positioned near the bottom thereof for containing a small amount of liquid to be nebulized;
    ultrasonic nebulizer means disposed below said reservoir means and said interaction chamber for nebulizing said small amount of liquid into an aerosol to be received by said interaction chamber;
    means positioned within said interaction chamber above said nebulizer means for initially maintaining the position of said aerosol therebelow for increasing the concentration thereof and for causing the larger particles of said aerosol to be impacted thereon and thereby be recovered by renebulization;
    outlet conduit means in communication with said interaction chamber for receiving said aerosol and including means for delivering same to the patient upon commencement of inspiration by said patient; and
    air inlet conduit means in communication with said interaction chamber including means for providing air flow behind said aerosol after commencement of inspiration by said patient.

2. The nebulization system as set forth in claim 1, wherein said outlet conduit means includes means for permitting said aerosol to be drawn therethrough only upon inhalation by said patient.

3. The nebulization system as set forth in claim 1 wherein said aerosol position maintaining means and said larger particle impacting means comprises an impaction sphere positioned in the central portion of said interaction chamber above said reservoir means.

4. The nebulization system as set forth in claim 3 wherein said interaction chamber comprises a substantially cylindrical vertically oriented tubular member having an upper opening and a lower opening, said impaction sphere being concentrically positioned near said upper opening.

5. The nebulization system as set forth in claim 4 wherein said inlet conduit means is disposed transversely to said interaction chamber.

6. The nebulization system as set forth in claim 5, further comprising flow control means positioned within said inlet conduit means for permitting only one-way flow of air into said interaction chamber therefrom.

7. The nebulization system as set forth in claim 6 wherein said reservoir means comprises an interface nozzle connected to and extending downwardly from the lower opening of said interaction chamber, and thin membrane means for covering the opening of said nozzle and for retaining the fluid to be nebulized therein.

8. The nebulization system as set forth in claim 7 further comprising means for retaining said thin membrane means over said opening of said nozzle.

9. The nebulization system as set forth in claim 8 wherein said membrane retaining means comprises a ring member positioned about said interaction chamber by having an aperture formed therein which is sized to fit about the circumference of said interaction chamber, said membrane being fitted between said ring member and said chamber.

10. The nebulization system as set forth in claim 9 further comprising injection inlet conduit means in communication with said interaction chamber for providing measured quantities of fluid to be dispensed to said reservoir means.

11. The nebulization system as set forth in claim 1 further comprising a Y-tube connector having three arms, one of which comprises the patient's mouthpiece, a second of which is connected to said outlet conduit means, the third of which is connected to exhaust means for receiving the exhalations of the patient.

12. Apparatus comprising, in combination:
an ultrasonic nebulizer for generating an aerosol bolus;
nebulization chamber means positioned above said ultrasonic nebulizer for receiving said aerosol bolus and for transmitting same to a patient to be treated;
impaction sphere means located within said nebulization chamber means in the path of said aerosol bolus for increasing the concentration thereof by maintaining the position of said aerosol bolus below said impaction sphere means until commencement of inspiration by said patient; and
means communicating with said nebulization chamber for directing air behind said aerosol bolus to said patient after commencement of inspiration by said patient.

13. The apparatus as set forth in claim 12 further comprising air inlet means connected to said nebulization chamber means so as to be located downstream of said aerosol bolus after formation thereof.

14. The apparatus as set forth in claim 13 further comprising one-way valve means positioned in said nebulization chamber means and activated by the inhalation of said patient to initially draw said aerosol bolus thereto followed by air from said air inlet means.

15. The apparatus as set forth in claim 14 wherein said nebulization chamber means comprises interface means including a thin membrane at the lower most position thereof for acting as a reservoir for the fluid to be nebulized and for transducing the sound wave generated by said ultrasonic nebulizer in order to nebulize said fluid into said aerosol bolus.

16. A nebulization system adapted to provide a compact aerosol bolus for inhalation therapy of a patient to be treated, which comprises:
an interaction chamber having a reservoir means positioned near the bottom thereof for containing a small amount of liquid to be nebulized;
ultrasonic nebulizer means disposed below said reservoir means for nebulizing said small amount of liquid into an aerosol;
means positioned within said interaction chamber for initially maintaining the position of said aerosol therebelow for increasing the concentration thereof by forming a more compact aerosol bolus; and
outlet conduit means for receiving said compact aerosol bolus and delivering same to the patient.

* * * * *